United States Patent
Seppa et al.

(10) Patent No.: US 8,850,893 B2
(45) Date of Patent: Oct. 7, 2014

(54) DEVICE FOR MEASURING PRESSURE, VARIATION IN ACOUSTIC PRESSURE, A MAGNETIC FIELD, ACCELERATION, VIBRATION, OR THE COMPOSITION OF A GAS

(75) Inventors: Heikki Seppa, Espoo (FI); Teuvo Sillanpää, Espoo (FI)

(73) Assignee: Valtion Teknillinen Tutkimuskeskus, Espoo (FI)

(*) Notice: Subject to any disclaimer, the term of this patent is extended or adjusted under 35 U.S.C. 154(b) by 794 days.

(21) Appl. No.: 12/746,342

(22) PCT Filed: Dec. 4, 2008

(86) PCT No.: PCT/FI2008/050709
§ 371 (c)(1),
(2), (4) Date: Jun. 4, 2010

(87) PCT Pub. No.: WO2009/071746
PCT Pub. Date: Jun. 11, 2009

(65) Prior Publication Data
US 2010/0275675 A1    Nov. 4, 2010

(30) Foreign Application Priority Data

Dec. 5, 2007  (FI) .................................... 20075879
Jun. 6, 2008  (FI) .................................... 20085563

(51) Int. Cl.
*G01N 29/036* (2006.01)
*G01P 15/08* (2006.01)
*G01L 9/00* (2006.01)
*G01L 11/06* (2006.01)
*G01R 33/028* (2006.01)

(52) U.S. Cl.
CPC ............ *G01L 11/06* (2013.01); *G01P 15/08* (2013.01); *G01N 29/036* (2013.01); *G01L 9/0041* (2013.01); *G01R 33/0286* (2013.01); *G01N 2291/0215* (2013.01)
USPC ............................... 73/579; 73/24.06

(58) Field of Classification Search
USPC ................ 73/24.01, 24.06, 37.5, 579, 584, 73/514.01, 504.12; 310/343
See application file for complete search history.

(56) References Cited

U.S. PATENT DOCUMENTS 4,194,510 A * 3/1980 Proudian ..................... 600/445
5,020,977 A * 6/1991 Lucas ........................... 417/322
(Continued)

FOREIGN PATENT DOCUMENTS

GB   2146123 A    4/1985
JP   2007-160435 A    6/2007
(Continued)

OTHER PUBLICATIONS

Granstedt et al. Abstract and Figures of "Modelling of an Electroacoustic Gas Senstor," Sensors and Actuators B: Chemical, vol. 104, Issue 2, pp. 308-311, Jan. 24, 2005.
(Continued)

*Primary Examiner* — David A Rogers
(74) *Attorney, Agent, or Firm* — Birch, Stewart, Kolasch & Birch, LLP

(57) ABSTRACT

The invention relates to a sensor (1) and a method for measuring pressure, variation in sound pressure, a magnetic field, acceleration, vibration, or the composition of a gas. The sensor (1) comprises an ultrasound transmitter (2), and a cavity (4) arranged in connection with it. According to the invention, the sensor (1) comprises a passive sensor element (3, 3') located at the opposite end of the cavity (4) to the ultrasound transmitter (2), the distance of which from the ultrasound transmitter (2) is selected in such a way that the resonance condition is met at the ultrasound frequency used, the ultrasound transmitter (2) comprises a light-construction diaphragm oscillator (9), which is thus well connected to the surrounding medium, and the sensor includes means for measuring the interaction between the ultrasound transmitter (2) and the cavity (4).

28 Claims, 5 Drawing Sheets

(56) References Cited

U.S. PATENT DOCUMENTS

| | | | |
|---|---|---|---|
| 5,167,124 A * | 12/1992 | Lucas | 62/6 |
| 5,185,728 A * | 2/1993 | Gilchrist | 367/163 |
| 5,315,565 A * | 5/1994 | Brosow | 367/140 |
| 5,386,714 A * | 2/1995 | Dames | 73/24.05 |
| 5,500,599 A * | 3/1996 | Stange | 324/634 |
| 5,524,477 A | 6/1996 | Wajid | |
| 5,622,180 A | 4/1997 | Tammi et al. | |
| 5,697,346 A * | 12/1997 | Beck | 123/494 |
| 5,733,670 A * | 3/1998 | Takeuchi et al. | 156/89.12 |
| 5,768,937 A * | 6/1998 | Wajid et al. | 73/24.06 |
| 5,872,309 A * | 2/1999 | Pinter | 73/49.3 |
| 5,983,727 A | 11/1999 | Wellman et al. | |
| 6,004,644 A * | 12/1999 | Takeuchi et al. | 428/47 |
| 6,168,680 B1 * | 1/2001 | Takeuchi et al. | 156/89.11 |
| 6,272,921 B1 * | 8/2001 | Ivanovich et al. | 73/290 V |
| 6,328,696 B1 * | 12/2001 | Fraser | 600/459 |
| 6,338,284 B1 * | 1/2002 | Najafi et al. | 73/866.1 |
| 6,426,582 B1 * | 7/2002 | Niederer et al. | 310/309 |
| 6,983,654 B2 * | 1/2006 | Balin et al. | 73/290 V |
| 6,999,596 B2 * | 2/2006 | Hiramoto et al. | 381/369 |
| 7,135,869 B2 * | 11/2006 | Sergoyan et al. | 324/636 |
| 7,146,857 B2 * | 12/2006 | Hok | 73/579 |
| 7,701,110 B2 * | 4/2010 | Fukuda et al. | 310/309 |
| 7,800,189 B2 * | 9/2010 | Caliano et al. | 257/419 |
| 2002/0013527 A1 * | 1/2002 | Hoek et al. | 600/437 |
| 2004/0085858 A1 | 5/2004 | Khuri-Yakub et al. | |
| 2004/0119591 A1 * | 6/2004 | Peeters | 340/539.26 |
| 2004/0129056 A1 * | 7/2004 | Hok et al. | 73/24.06 |
| 2004/0211260 A1 * | 10/2004 | Girmonsky et al. | 73/579 |
| 2005/0075572 A1 * | 4/2005 | Mills et al. | 600/459 |
| 2005/0109080 A1 | 5/2005 | Hok | |
| 2005/0146240 A1 | 7/2005 | Smith et al. | |
| 2005/0231067 A1 * | 10/2005 | Cook et al. | 310/313 R |
| 2005/0288590 A1 | 12/2005 | Kaplan | |
| 2006/0043843 A1 * | 3/2006 | Sugiura et al. | 310/348 |
| 2006/0260929 A1 * | 11/2006 | Hirabayashi et al. | 204/157.42 |
| 2007/0059858 A1 * | 3/2007 | Caronti et al. | 438/50 |
| 2007/0164632 A1 * | 7/2007 | Adachi et al. | 310/311 |
| 2007/0190680 A1 | 8/2007 | Fukuda et al. | |
| 2008/0073998 A1 | 3/2008 | Sugiura et al. | |
| 2008/0169921 A1 * | 7/2008 | Peeters | 340/539.11 |
| 2009/0200101 A1 * | 8/2009 | Baker et al. | 181/148 |
| 2009/0301199 A1 * | 12/2009 | Azuma et al. | 73/603 |
| 2011/0057541 A1 * | 3/2011 | Cho et al. | 310/322 |

FOREIGN PATENT DOCUMENTS

| | | |
|---|---|---|
| JP | 2007-222990 A | 9/2007 |
| NO | 323259 B1 | 2/2007 |
| WO | WO 98/29721 A | 7/1998 |
| WO | WO 2007/096636 A1 | 8/2007 |

OTHER PUBLICATIONS

Granstedt et al., Abstract and Figures of "Gas Sensor with Electroacoustically Coupled Resonator," Sensors and Actuators B: Chemical, vol. 78, Issues 1-3, pp. 161-165, Aug. 2001.

\* cited by examiner

DEVICE FOR MEASURING PRESSURE, VARIATION IN ACOUSTIC PRESSURE, A MAGNETIC FIELD, ACCELERATION, VIBRATION, OR THE COMPOSITION OF A GAS

The present invention relates to an apparatus, according to the preamble to Claim 1, for measuring pressure, variation in acoustic pressure, a magnetic field, acceleration, vibration, or the composition of a gas.

The invention also relates to a method for measuring pressure, variation in acoustic pressure, a magnetic field, acceleration, vibration, or the composition of a gas.

1. General

In micromechanical pressure sensors, microphones, etc., the distance between two diaphragms is measured in a so-called capacitive manner. This can be done by measuring the voltage induced by movement, or by measuring the capacitance at a high frequency. Because the diaphragms are very close to each other, this leads to several problems: the diaphragms adhering to each other, movements caused by the thermal expansion of the base and a component, etc. In addition to mechanical problems, present constructions suffer from the fact that the impedance between the two diaphragms is high, and that all the electrical leaks cause problems.

In mobile telephones, a changeover is presently being made to micromechanical microphones. MEMS pressure sensors have already become generally used, for example, in watches. In terms of the MEMS construction, they are very similar. They differ only in packaging technique, selection of materials, electronic solutions, etc., but are nevertheless based on the same basic principle: measurement of the distance between two diaphragms located close (1 μm-3 μm) to each other. These are referred to as first-generation MEMS microphones and pressure sensors. The present new invention eliminates several weaknesses of the first-generation sensors and makes possible a stable MEMS sensor for measuring several variables, which can be easily attached to a circuit card. Present gas sensors are either chemical or optical.

Chemical sensors have poor stability, and optical sensors are expensive for mass applications.

A solution is known from U.S. Pat. No. 323,259, in which an ultrasound transceiver, made using MEMS technology, is located in a tuned cavity. With the aid of the transceiver, the speed of sound in a gas is measured, and the properties of the gaseous substance are determined based on the speed of sound. The device has the drawback of a complicated construction, which demands two active elements to be formed, together with circuitry. The complexity increases manufacturing costs.

A gas-sensor application, in which a piezo-ultrasound transmitter is used, is known from the publication "Modelling of an electroacoustic gas sensor", F. Granstedt, M. Folke, M. Ekström, B. Hök and Y. Bäcklund, Sensors and Actuators B 104 (2005) 308-311.

A gas-sensor application, in which a piezo-ultrasound transmitter is used, is also known from the publication "Gas sensor with electroacoustically coupled resonator", F. Granstedt, M. Folke, B. Hök and Y. Bäcklund, Sensors and Actuators B 78 (2001) 161-165.

Because a piezo-ultrasound transmitter is based on the radiation of a fixed oscillator, its connection to the gas is weak, in other words, the changes taking place in the gas or oscillation chamber appear faintly in the input impedance of the ultrasound transmitter, or correspondingly as a function of the changes in the power that it draws. In the articles referred to, only the speed of gas in a cavity is measured, no reference being made to the measurement of the location of a passive sensor diaphragm, based on a single active component.

The present invention is intended to eliminate the drawbacks of the prior art and permit the same construction to also be used to make measurements of gases, based on the speed and damping of sound. In addition, the sensor can be used for the measurement of both a magnetic field and acceleration.

The invention is characterized by what is stated in the characterizing portions of the claims.

The sensor is based on an ultrasound transmitter, which preferably comprises a light-construction oscillation source in the form of a diaphragm and an ultrasound cavity arranged on top of it, the dimensions of which are arranged to resonate at the operating frequency of the ultrasound transmitter. Typically one of the main dimensions of the cavity is dimensioned to be a quarter, a half, or a multiple of these, of the wavelength of the ultrasound.

By measuring the impedance of the ultrasound through the input impedance or input power of the transmitter, the impedance will be observed to be strongly dependent on the deviation of the cavity above it relative to the aforementioned length. If operation takes place in the series resonance of the ultrasound, small changes in the impedance of the transmitter will be directly proportional to the height of the cavity and the width of the resonance will be proportional to the air damping in the cavity. The geometry of the sensor is arranged in such a way that the variable being measured affects the length of the cavity.

More specifically, the sensor according to the invention is characterized by what is stated in the characterizing portion of Claim 1.

For its part, the method according to the invention is characterized by what is stated in the characterizing portion of Claim 12.

Considerable advantages are gained with the aid of the invention. Compared to capacitive constructions, the electronics can be effectively shielded, because electrical contacts are not required to the diaphragm or surface acting as the sensor element. Thus, the sensor can be brought into direct contact with the measurement object. In some preferred embodiments of the invention, even mechanical contact with the surface being measured is possible.

Compared to the piezo-crystal ultrasound sources described above as the prior art, a significant improvement in sensitivity is achieved, because the light-construction diaphragm ultrasound transmitter according to the invention connects about 10 times better to the medium being measured, this being apparent directly in the sensitivity of the measurement. At the same time, a significant cost advantage is achieved through the fabrication technique, because the sensor structure can be integrated, for example, in the same SOI structure.

Compared to the MEMS construction described, a significant advantage is achieved in the simplification of the device. Only one active element is required, with the aid of which the most diverse measuring elements can be created.

In the following, the invention is examined with the aid of examples and with reference to the accompanying drawings.

Figure 1A:
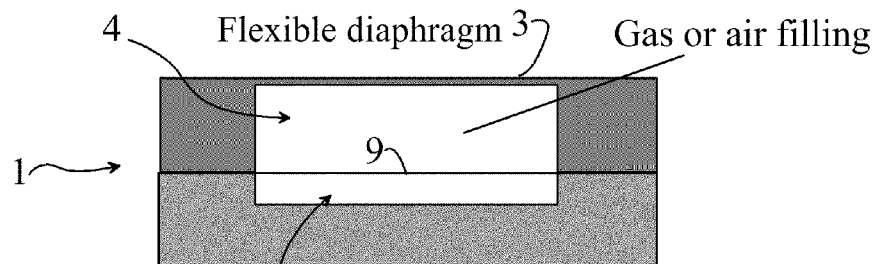
FIGS. 1a and 1b and 1c show cross-sectional side views of alternative basic constructions of the sensor.
Figure 1B:
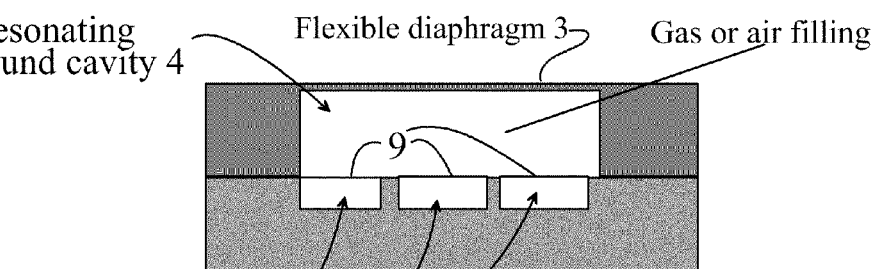
Figure 1C:
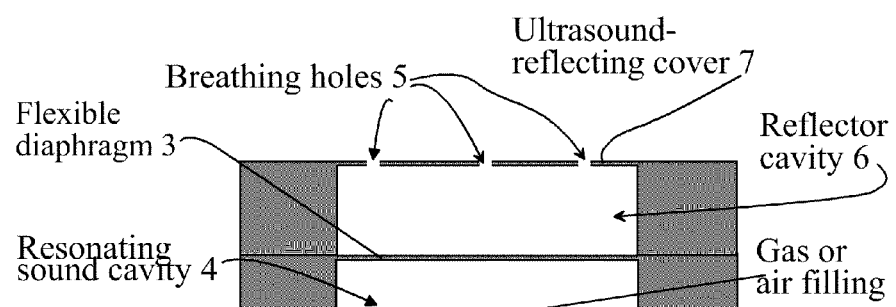

FIGS. 1a and 1b show the schematic construction of the ultrasound sensor 1 according to the invention. In FIG. 1a there is a construction, in which the ultrasound transmitter 2 is formed of a single cavity and in 1b there is a situation, in which sound is created using several oscillations transmitters 2 in parallel. The diaphragm 9 of the transmitter 2 creates a resonating ultrasound in a cavity 4 above it. The ultrasound transmitter 2 creates both electrical series and parallel resonance. The impedance of the series resonance is typically 1-10 kΩ and the impedance of the parallel resonance is 10-100-times greater, always according to the quality factor of the resonator. It can be assumed that the flexible upper diaphragm 3 will reflect most of the sound back and only a small part will radiate out behind the diaphragm 3. In practice, this means that the impedance of the series resonance diminishes. If the diaphragm radiates power out, the quality factor of the cavity diminishes and the resolution decreases. FIG. 1c shows a way, in which an additional cavity 6, the size of half the wavelength, and the cover 7 of which is preferably thick and stiff to effectively reflect the wave of ultrasound back into the cavity, is added above the cavity.

Figure 2A:
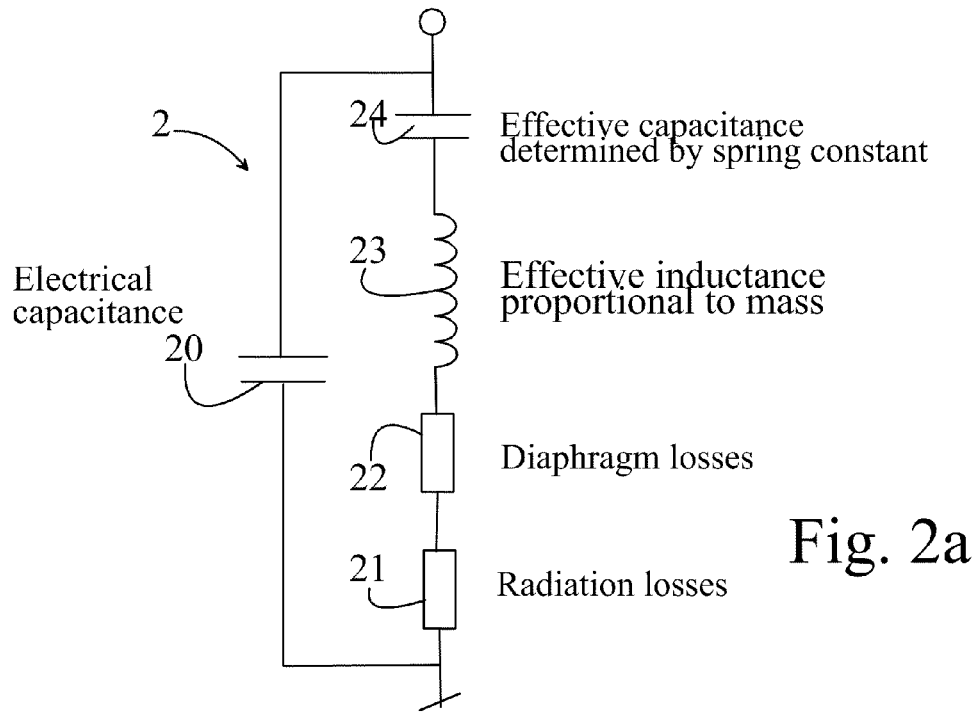
FIGS. 2a and 2b show schematically an electrical equivalent circuit of the sensor according to the invention.
Figure 2B:
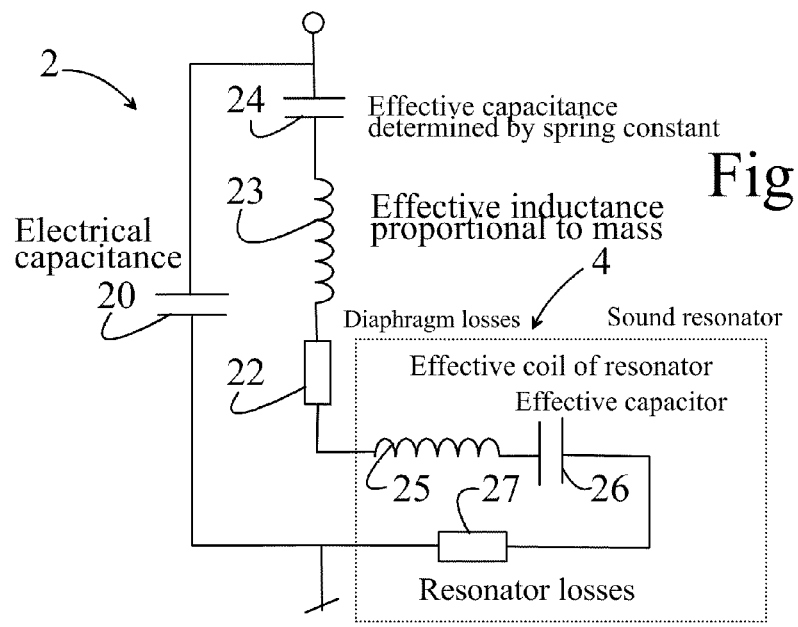

FIG. 2a gives the electrical equivalent circuit of the ultrasound transmitter 2. The coil 23 depicts the mass of the diaphragm 9 and the capacitance 24 its spring constant and capacitance 20 the electrical capacitance. The resistance 22 represents the diaphragm's losses and the resistance 21 the radiation losses. The values of the components are also dependent on the voltage over the ultrasound sensor. If the sound cavity is, for example, $\lambda/2$ in length, it will amplify the resonance of the ultrasound. The sound wave arrives at the ultrasound diaphragm in phase, which increases the movement of the diaphragm. FIG. 2b shows the electrical equivalent circuit with the cavity 4, when the cavity is $\lambda/2$ in length, i.e. the cavity forms a series resonance. It should be noted that the cavity could also be a quarter of the wave, or a multiple of it in length. The impedance of the cavity 4 replaces the radiation resistance 21 in FIG. 2a. Thus, the impedance of the cavity is formed from the effective coil 25 of the resonator 4, the effective capacitor 26, and the losses 27 of the resonator. We note that the system forms a single new series resonance. We can consider the resonances as degenerating to form a single resonance. If the effective capacitance 26 formed by the cavity 4 is now smaller than the effective capacitance 24 of the ultrasound transmitter 2, and if the inductance 25 of the cavity 4 is greater than the inductance 23 of the ultrasound sensor, the impedance of the sensor 1 (=transmitter 2+cavity 4) will be determined almost entirely by the cavity 4. In practice, the situation is not as ideal as this. In addition, we can assume that the internal losses of the ultrasound transmitter 2 are smaller than the losses created by the cavity 4. This can be achieved, if we use a micromechanical transmitter 2. It is not possible to create the situation in question using a piezo-active transmitter. Optimization requires the mass of the oscillating diaphragm 9 of our ultrasound transmitter 2 to be minimized and the spring constant (tension or stiffness) to be optimized in such a way that the desired resonance frequency is achieved. In addition, the surface area of the diaphragm 9 should be dimensioned to optimize the connection with the gas. The optimization depends on whether the diaphragm oscillates in piston mode or in flexible mode. In addition, the shape of the transmitter 2 is significant. The diaphragm 9 can also be formed from many small individual ultrasound diaphragms 9. This situation is shown in FIG. 1b. In general, the radiation optimum will be achieved when the width of the diaphragm 9 is about in the order of the wavelength of the ultrasound frequency used. I.e., the natural dimensions of the cavity 9 are typically: width $\lambda$ and height $\lambda/2$. The width can also be greater, if the transmitter is made from several separate elements. The location of the upper diaphragm 9 changes the phase of the impedance or, in other words, its imaginary part. The losses of the cavity 4 change the real part of the impedance. In other words, by using a phase-sensitive detector to measure the value of the imaginary part, we can determine the deviation of the diaphragm 9. I.e., as a point of departure the sensor 1 is a sensor that measures location or change in location, but which can be used to measure several different variables. Hereinafter we will refer to this sensor generally as the UtraSensor.

2. Applications

As a point of departure, the sensor 1 measures the location of the diaphragm, or the change in its location. This means that it can be used in all applications, in which precise measurement of the location of the surface is essential. In other words, the UtraSensor can be used to make a microphone, pressure sensor, acceleration sensor, or magnetometer. In addition, the device can be used to measure the speed of sound and the damping of a gas, i.e. it can be used as a gas sensor. If the cavity has the length of a quarter of a wavelength, and if it is filled with a gas that is heavier than air, it will form an impedance converter between the MEMS ultrasound transmitter and the air. In the following, the special features of various sensors are reviewed.

2.1 Location Sensor

The UtraSensor is, as such, a sensor that measures location, velocity, or acceleration. Acoustic emissions are typically measured by connecting a piezo-active structure to the surface of a metal, to detect acoustic waves. In this application, the UtraSensor can be used directly to replace piezo sensors. The UtraSensor has the advantages of a smaller size and price and the possibility of integrating several receivers on the same silicon substrate. Of course, the location sensor can be used as a normal ultrasound sensor and transmitter, for instance, in ultrasound imaging devices.

2.2 Impedance-Matched Broadband Ultrasound Transmitter and Receiver.

If we make the height of the cavity equal to one quarter of the wave, and we fill it with a suitable gas mixture (e.g. argon and carbon dioxide, nitrogen, . . . ), we can adjust the gas density in such a way that the specific impedance of the micromechanical transmitter completely matches air. This takes place in practice, if the density of the gas in the cavity is about ten times greater than that of air. In practice, the gases, which can be used, and the density of which is significantly greater than that of air, are Argon and $CO_2$. Benzene can also be used. This solution would make possible, for example, a radar based on ultrasound that is better than existing ones (e.g., parking radar for cars), a velocity meter for gases, etc. In addition, because the electronics can be taken far from the subject being measured, it permits measurement in difficult conditions (e.g., a temperature of 300 degrees Celsius). Nowadays, the radiation efficiency from a MEMS source to air is reasonably good (1%-3%) compared, for example, to a piezo-active crystal. Piezoactive plastics are almost as good as MEMS. By adding a gas converter according to the present invention, the efficiency could be raised to well over 10% and the signal-noise ratio can thus be improved significantly. For example, the flow measurement of gases by means of ultrasound would be made significantly more accurate, because we could manufacture a sensor with a broader band and greater phase stability.

2.3 Gas Sensor

The sensor can be used to measure both the speed and damping of sound in a gas. The gas can be determined based on these. Of course, the speed and damping of sound also depend on temperature and humidity, so that an accurate measurement requires the measurement of the said variables. In the case of a gas sensor, the resolution of the sensor is not a bottleneck, but the important errors arise from mechanical stress, temperature compensation, etc. Of course, it is important to note that the sensor does not provide unequivocal information on the composition of a gas. If, however, we can use the sensor at higher frequencies too, we can use the changes in the speed and damping of sound to obtain additional information on the composition of the gas. It is generally known that, by measuring both the speed and damping of sound over a very broad frequency range, the humidity of the air, for example, can be determined separately.

Depending on the power used, the gas in the cavity of the sensor will heat up (1-3 C.°). If the gas is very humid, the losses of the cavity will increase and the heating power will increase to evaporate off the moisture. On the other hand, ultrasound reduces the surface tension of the droplets, which then gasify and do not remain on the surfaces. In other words, the method makes it possible to affect the humidity of the gas in the cavity.

Because the sensor is not particularly selective, it is most suitable for the detection of an individual gas. It could be, for example, an automobile carbon-dioxide sensor—in the future perhaps a hydrogen sensor, if the use of hydrogen becomes widespread in automobiles—or as a gas detector in buildings or industry. The sensor is particularly suitable as a leak sensor in valves. This is because a valve controls a known gas and the sensor can be located close to the valve in a closed space, where the content of the gas prior to the leak is nearly unchanging. In this application, simultaneous temperature measurement will be sufficient to compensate for errors. Of course, the sensor can act as part of a sensor system, in which a few gases are measured specifically and a missing gas can be detected using the method described. In a gas sensor, the upper diaphragm can be made very stiff and heavy and thus the ultrasound can be made to reflect well from the under surface of the diaphragm. For example, a SOI-based cavity is highly suitable for this purpose. In connection with a gas sensor, we use the name the UtraGas or the UtraGas Sensor.

2.4 Pressure Sensor

If the sensor is used for measuring pressure, the cavity should be filled with a known gas. Preferably with a gas with low sound damping and which causes a small effective capacitance and large inductance. Of course, the gas should also be selected so that it will not easily react with silicon or silicon oxide, and will not easily diffuse out of the cavity. A problem with existing MEMS pressure sensors is that the spring constant must be dimensioned in such a way that the height of the cavity will be sufficiently stiff for the maximum pressure not to cause excessive deflection in the diaphragm. The height of the cavity must be kept low, so that capacitive measurement can be made using a low voltage, while the resolution nevertheless remains sufficient. In the UltraSensor this problem does not appear. In other words, by dimensioning the diaphragm to be slack, we increase sensitivity and thus make the device less sensitive to, for example, problems arising from torsion in the substrate. Of course, the downside is that the UltraSensor's effective spring constant depends to some extent on the pressure, according to the following equation $$k = k_m + \frac{pA}{h}$$

in which h is the height of the cavity, p the pressure, and A the cross-sectional area of the cavity. By substituting typical values in the equation, it will be noticed that, when the height is 100 μm or greater, the mechanical spring constant determines the effective spring constant. Thus, the pressure dependence of the spring constant does not cause any great problem.

The UtraSensor's great dynamics distinguishes it essentially from present capacitive MEMS sensors, in which the distance of the electrodes from each other is only a few micrometers. In a construction of this kind, so-called capacitive non-linearity arises, which, of course, can be improved by means of feedback. However, feedback often requires a high DC voltage, which is difficult to produce and which causes charging of the surfaces and thus instability. Non-linearity is also caused by the non-linearity of the spring. We call the pressure sensor the UtraPress.

Though the present MEMS pressure sensor is reasonably good, the UtraSensor can provide a cheaper and more stable MEMS sensor for many applications. It is cheap because the increase in sensitivity allows us to fabricate a smaller sensor and, on the other hand, the sensor does not require a special packaging technique, because we measure low impedance, the IC need not be located close to the sensor. Its dynamics and linearity are also superior to present capacitive MEMS sensors. In the case of a pressure sensor, we also do not analyze its sensitivity, as in any case this is sufficient in practical applications. If the sensitivity is not sufficient, we can also use the construction according to FIG. 1c to improve the sensitivity. In FIG. 1c, a second cavity, the reflection cavity 6, which is connected to the measurement subject with the aid of holes 5 made in the reflective cover 7, is formed above the sensor cavity 4. This construction is used to eliminate the ultrasound penetrating the sensor structure to the external air space, which has penetrated the diaphragm 3. Measurement inaccuracies are determined in the pressure sensor mainly by systematic errors and problems caused by the package.

2.5 Magnetometer.

If we manufacture a coil, in which either direct current or alternating current travels, on top of the diaphragm, we make the diaphragm to either move or oscillate as a function of the external magnetic field. In the case of direct current, the device operates in exactly the same way as a pressure or gas sensor. We measure the impedance of the change. If, on the other hand, we use alternating current and we tune the upper diaphragm to resonate with this frequency, we create impedance modulation, which appears as sidebands of the carrier wave. If we make a very open and breathing diaphragm, we can make the Q value of the low-frequency resonance very large, and in this way we can maximize the sensitivity of the device. The magnetometer can be combined with a gas or pressure sensor. A problem in the sensor is that, in a simple form it measures only one component of the magnetic field. Due to the gas damping, the dissipation, and through it noise, is greater than that of a traditional MEMS sensor, but on the other hand the spring constant can be made very small, and in this way sensitivity can be maximized. We reckon that the UtraSensor can be manufactured as a product with a sensitivity that can compete with that of present magnetometers. However, because its impedance is low, the electronics can be taken far from the magnetometer. This permits its use in difficult conditions, where electronics cannot be kept close to the measurement object. It can be used, for example, in fusion power plants. The same is true of the magnetometer as of the pressure sensor: it has a wide dynamic range. A magnetometer can also be made by making the upper diaphragm of a magnetic material. We call this invention the UtraMag.

2.6 Acceleration and Vibration Sensor

If the structure breathes sufficiently, and if the mass of the upper diaphragm is made large, we can use the method to build an acceleration sensor. With the aid of the spring constant and the mass, we can adjust the sensitivity and upper-limit frequency of the sensor. Because the spring constant can be very weak, we can manufacture a sensor that is considerably more sensitive than present acceleration sensors. The sensitivity can be calculated from Equation 3 in the present publication. The motion is determined from the equation kx=ma, in which a is acceleration. The damping of the upper diaphragm can be regulated using perforation of the diaphragm. Generally, an acceleration sensor is dimensioned to be over-damped.

Figure 3:
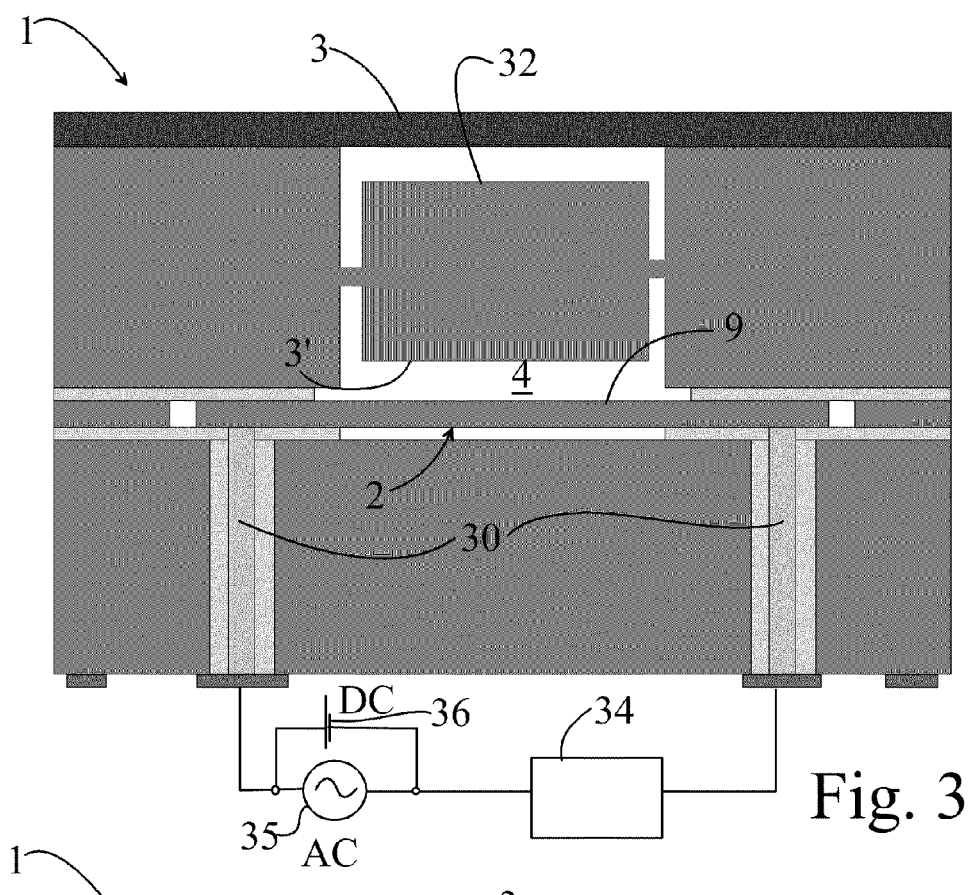
FIG. 3 shows a cross-sectional side view of the construction of an acceleration sensor according to the invention.

The greatest benefit of the acceleration sensor is the wide dynamic range of the UtraSensor. In many measurement subjects, there are a considerable number of vibrations of different frequencies and amplitudes, or high frequency 'squeaking'. Due to the capacitive non-linearity, distortion and intermodulation distortion (the mixing of different frequency components with each other) appear in present MEMS sensors. These cannot be eliminated afterwards. Of course, non-linearity also causes foldover in the noise. This cannot be eliminated afterwards with post-filtering or computation. FIG. 3 shows an acceleration or vibration sensor with high resolution and wide dynamics. In the solution, the under surface 3' of the mass 32 acts as the primary sensor element. The closed construction presents moisture affecting the acceleration sensor and the upper stiff diaphragm 3 reflects the power back to the cavity 4, thus increasing the sensitivity of the sensor. The sensor is also not sensitive to pressure variations. By using several ultrasound transmitters and suitably patterning the mass 32, we can also measure lateral movements, i.e. make an x and y-direction acceleration sensor. In this case, it is preferable for the upper cavity to be the length of one quarter of a wave. We call this sensor the UtraVib. FIG. 3 also shows, in a simplified form, the electronics suitable for the invention, in which an alternating electricity source 35 is used between the electrodes 30 of the ultrasound transmitter 2 and, if necessary, direct-voltage biasing 36 in parallel or series with this. The variable being measured is obtained by impedance measurement using the block 34 between the electrodes 30, this being shown in greater detail in FIG. 6. Thus, block 34 is used to measure the impedance of the ultrasound transmitter 2, with the aid of its input current and voltage.

2.7 Microphone.

Perhaps the most important application of the UtraSensor is a microphone. This is because it provides a considerably more robust way than present ones of making a precise measurement of the movement of the diaphragm. On the other hand, it is entirely MEMS-based and thus permits a cheap fabrication technique. In this connection, we call the sensor the UtraMic.

It is assumed that the connection of the ultrasound sensor to the sound resonator is so large that the impedance is determined by the effective coil of the resonator, the capacitor, and the losses of the cavity. If we use phase measurement to measure the effective capacitance of the resonance circuit, we can write the resolution in the following form.

$$\left(\frac{\Delta x}{x}\right)^2 = \left(\frac{\Delta L}{L}\right)^2 = \left(\frac{\Delta C}{C}\right)^2 = \frac{1}{\omega Q} \frac{2k_B T}{CU^2} \quad (1)$$

Here k is the Boltzmann constant, Q the quality factor of the resonance circuit, T the gas temperature, $\omega$ the angular frequency of the ultrasound, $\omega=2\pi f$, in which f is the frequency), and U the measuring frequency used in the measurement. It should be noted that C is the effective capacitance, which depicts the ultrasound energy stored in the gas. The effective capacitance of the ultrasound transmitter is determined, biased by direct voltage, from the equation $$\frac{1}{C} = \frac{1}{k}\left(\frac{U_0}{2\omega_0}\right)^2 - \frac{1}{C_0} \quad (2)$$

in which $\omega_0$ is the mechanical resonance frequency, k the spring constant, $C_0$ the electrical capacitance, and $U_0$ the bias voltage. The inductance is correspondingly obtained from the equation $$L = m\left(\frac{U_0}{2\omega_0}\right)^2$$

in which m is the mass of the diaphragm. The spring constant can naturally be depicted with the aid of the mass and resonance frequency, as follows.

$$k=(2\pi f_m)^2 m \quad (2)$$

The movement of the diaphragm is directly proportional to the pressure and the effective surface area of the diaphragm. We can now write the pressure in the form of the resolution $$(\Delta p)^2 = \left(\frac{k\Delta x}{A}\right)^2 \quad (3)$$

$$= \frac{1}{\omega Q}\frac{2k_B T}{CU^2}\left(\frac{k}{A}\right)^2 x^2$$

$$= \frac{1}{\omega Q}\frac{2k_B T}{CU^2}\left(\frac{(2\pi f_m)^2 m}{A}\right)^2 x^2$$

If we operate in a resonance, $x=\lambda/2=v/2f$, in which v is the speed of sound in air (v=340 m/s), we can now write the pressure resolution in the form $$(\Delta p)^2 = \frac{1}{\omega Q}\frac{2k_B T}{CU^2}(2\pi^2 f_m h\eta v)^2 \quad (4)$$

in which $\eta$ is the density of the cavity's diaphragm and h is its thickness.

It will be noted from the equation, that the resolution can be adjusted mainly by means of the volume of the sound (in this case U), the surface area, and by making the diaphragm as thin as possible. The angular frequency of the ultrasound and the input of the resonance are constant, because the damping of the air per unit of length is directly proportional to the frequency. The effective capacitance C is proportional to the surface area of the cavity, so that the width of the cavity is a linear way to adjust the sensitivity of the microphone. If the width must be made greater than the wavelength of the ultrasound, it is better to divide the ultrasound transmitter into several cavities, which will facilitate the dimensioning of the transmitter. Because the width of the microphone's band must be about 20 kHz, we can only dimension it to be as close as possible to the required band. In this case, the noise temperature T is about 300 K, because the amplifier can be easily designed in such a way that its noise temperature is well below room temperature. We can also write the equation with the aid of the density η and thickness h of the diaphragm, as stated in the equation. If we assume that $\omega Q = 500 \times 10^5$, $f = 10$ kHz, $C = 1.0$ pF, $h = 1$ μm, $\eta = 5 \times 10^2$ kg/m³, and $U = 3$V, m=we obtain 30 μP/Sqrt (Hz) as the pressure resolution. This is sufficient for a practical microphone. Of course, this is an ideal situation, in which the sound resonator by itself determines the losses of the entire construction. If we assume that the impedance of the ultrasound resonator is 3 kΩ, the power consumption will be about 1 mW, which is reasonably large for a microphone, but acceptable.

In an ideal situation, the resolution of the microphone is sufficient, but in practice we may have to widen surface area of the cavity to be greater than the wavelength, in order to increase sensitivity. However, we may have to use the construction shown in FIG. 1c, to reduce ultrasound losses. Though the UltraMic appears to permit a sufficiently sensitive microphone, optimization must be performed very carefully. After optimization, the equation states that only an increase in the width of the cavity, or an increase in voltage will permit a more sensitive microphone to be made.

We have presented a method, with the aid of which changes in sound pressure can be measured at a very high resolution, using a micromechanical ultrasound transmitter. The advantages of the solution are its small size, the independence of the electronics from the sensor, and moisture tolerance. Further, the structure also need not be protected against adhesion of the diaphragm and can be placed directly on a circuit card without a separate package. The challenges of the construction are the adjustment of the manufacturing parameters, the temperature dependence of the sensitivity, and increased power consumption. Of the applications of the invention, the microphone UtraMic is highly reminiscent of an optical microphone, in which the location of the diaphragm is measured optically. In the sensor and method according to the invention there is, however, no need for optics, so that thus there are no surfaces sensitive to dirtying. Another challenge in the invention is how to design the upper diaphragm in such a way that it does not radiate ultrasound to the environment, thus reducing the quality factor of the cavity. This can, however, be avoided by placing a new breathable construction on top of the upper diaphragm, which reflects the power back to the cavity, according to FIG. 1c. The diaphragm 7 of this additional construction can be made so stiff that it cannot radiate ultrasound power out. Of course, this construction increases costs and thickens the component to some extent. This solution should be selected only if the resolution will otherwise not be sufficiently high.

2.8 Combination Sensors

Aforementioned combinations can be made from the Utra-Sensor. First, because the electronics need not be placed next to each sensor, we can make several sensors on one or separate silicon bases. The sensors can be read by, for example, utilizing multiplexing. Specific sensors can also be combined in such a way that the same sensor reads two variables. A low-frequency sensor (pressure, gas, magnetic-field sensor) can be combined with a high-frequency sensor (microphone, vibration sensor, and high-frequency acceleration sensor). For example, if in the sensor according to FIG. 1c, the upper diaphragm 7 too were to be flexible, and the intermediate diaphragm 3 reflective but also partly able to be penetrated by ultrasound, we could make the upper diaphragm 7 a pressure sensor and the middle diaphragm 3 an acceleration sensor. A gas sensor could be combined, for example, with the acceleration sensor, etc. In other words, if several different measurement variables are required in the same place, we can reduce the price of the entire sensor module by suitably combining sensors.

3. Electronics

The electronics are described with reference to FIG. 6, which shows the module 34 of FIG. 3 in greater detail. Because a micromechanical ultrasound transmitter 2 is used, it is possible to either bias the transmitter with a DC voltage 36 and create sound at the frequency f with the aid of an oscillator 35, or we can omit the DC biasing and create sound by using the frequency f/2. This is because the power is proportional to the square of the voltage. This is advantageous, because we can effectively eliminate crosstalk. In the measurement of the base impedance, we may need a bridge circuit, or compensation, in order that sufficient power amplification can be taken from the first amplifier stage. Because the frequency of the sound resonator depends on the temperature, the frequency should be adjustable. This means that we use an oscillator 35 controlled by voltage, which is locked with the aid of a phase-sensitive detector, in such a way that the impedance is real. In the case of a microphone, it is advantageous to make the regulation very slow (app. 10 Hz), in which case the signal proportional to the imaginary part of the phase-sensitive detector will be directly proportional to the location of the diaphragm at frequencies 10 Hz-20 kHz. In the case of a gas sensor and a pressure sensor, the regulating voltage required will tell the value of the variable being measured. In the case of a magnetometer, we can use the regulating voltage directly, or, if alternating current travels in the coil, we make the regulator slower than the frequency of the alternating current, when the magnetic field will be directly proportional to the amplitude of the modulation created.

Figure 6:
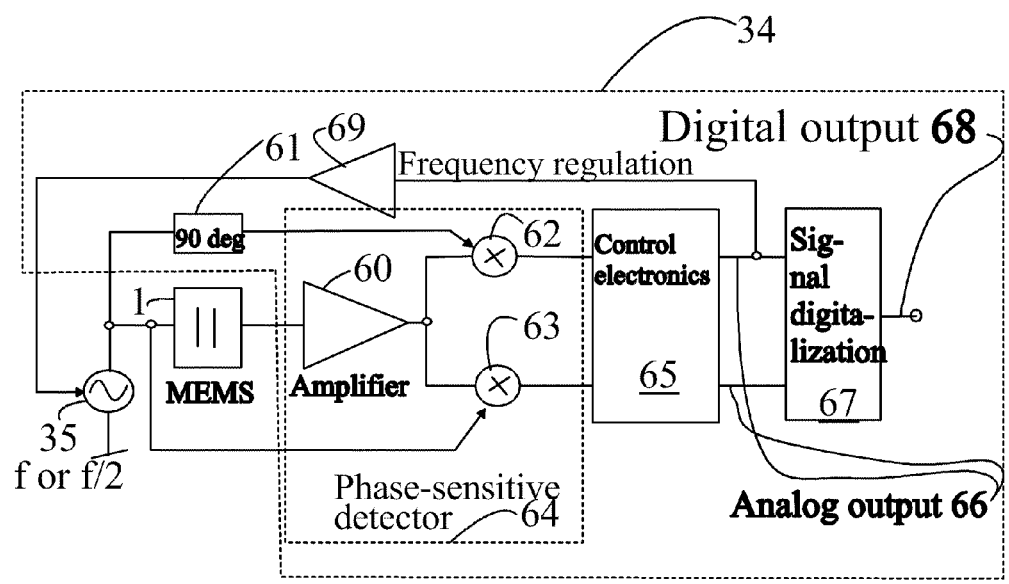
FIG. 6 shows schematically the electronics of the sensor according to the invention.

Thus, according to FIG. 6, the signal from the MEMS circuit 1 is led to the amplifier 60 of the circuit 34, the output of which is detected using phase-sensitive detectors 62 and 63. Both the component in phase and the component in a 90-degree phase shift are detected (quadrature detection) from the output. The component of the second branch of the phase detector is rotated through 90 degrees by a phase inverter 61. The signal obtained from the detectors 62 and 63 is processed by the control electronics 65. An analog output 66, which is led to the signal digitalization block 67, is also obtained from the control electronics 65. A digital output 68 is obtained from this circuit. Feedback from the frequency control 69 to the oscillator 35 is implemented from the control electronics 65.

An essential feature of the invention is that the measurement is normal measurement of the real and imaginary parts of a 300 Ohm-10 kOhm impedance, which can be easily implemented using a simple and cheap IC circuit. Precise measurement of temperature is essential only in the case of a pressure sensor. In a microphone, the dependence of the sensitivity on the temperature should be compensated. A gas sensor too will require temperature measurement and, in precise measurement, possibly also measurement of humidity. If we use f/2 running, we can use DC voltage to adjust the spring constant of the ultrasound sensor. This may be necessary, if the ultrasound transmitter's own resonance differs significantly from the sound resonator's own resonance. Too great a difference may lead to the resonances disintegrating into two separate resonances and in this way the regulation of the frequency may not necessarily function. The resolution will also be significantly reduced.

The parallel capacitance can be eliminated by placing the coil in series or parallel. If the coil is in series, the voltage over the ultrasound transmitter increases and we can increase the power of the ultrasound transmitter without using a high voltage. If we use a high current or voltage, we must make either a passive or an active bridge, in order to compensate the signal being measured. In active compensation, a signal with the opposite phase to the signal going to the sensor is summed with the signal coming from the sensor.

4. Fabrication

Figure 4:
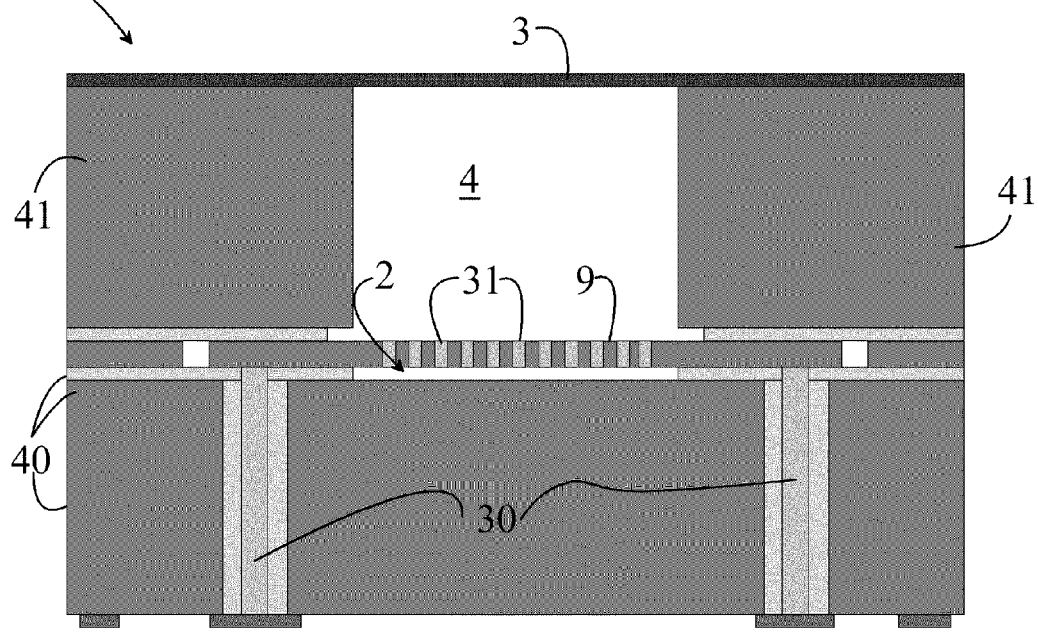
FIG. 4 shows a cross-sectional side view of details of the manufacturing process of the sensor according to the invention.

FIG. 4 shows a way to fabricate one component according to the invention. The ultrasound transmitter 2 is based on a SOI disc 40, the silicon-oxide structure of which is sacrificed in locally, through holes 31 made by RIE etching the disc. The holes 31 are finally filled with polysilicon. The cavity of the transmitter 2 is in a vacuum, so that the ultrasound losses will be determined only from the air, or in this case from the losses of the sound cavity 4. In this case, the electrical connection of the ultrasound resonator is made by growing a polysilicon column 30 in holes made by RIE etching. Before the column 30 is grown, the silicon walls are oxidized. The sound cavity 4 can be made in the disc structure, which is formed of a polysilicon layer 41 and a diaphragm 3. The layer 41 can also be of silicon nitride or amorphic metal. The cavity 4 can be made, for example, by RIE etching the structure 41, in which case the etching stops at the upper diaphragm 3. The discs 40 and 41, 3 can be joined together by fusion bonding. Finally, the disc is cut off, for example, by sawing. If a breather hole is required, it can be made in the upper diaphragm 3, the lower surface of the sound cavity, or the upper surface 9 of the ultrasound transmitter. The size of the breather hole determines lower-limit frequency and should be very low, especially in a microphone. In a high-speed gas sensor, it should be sufficiently large, in order to achieve a fast response time.

Figure 5:
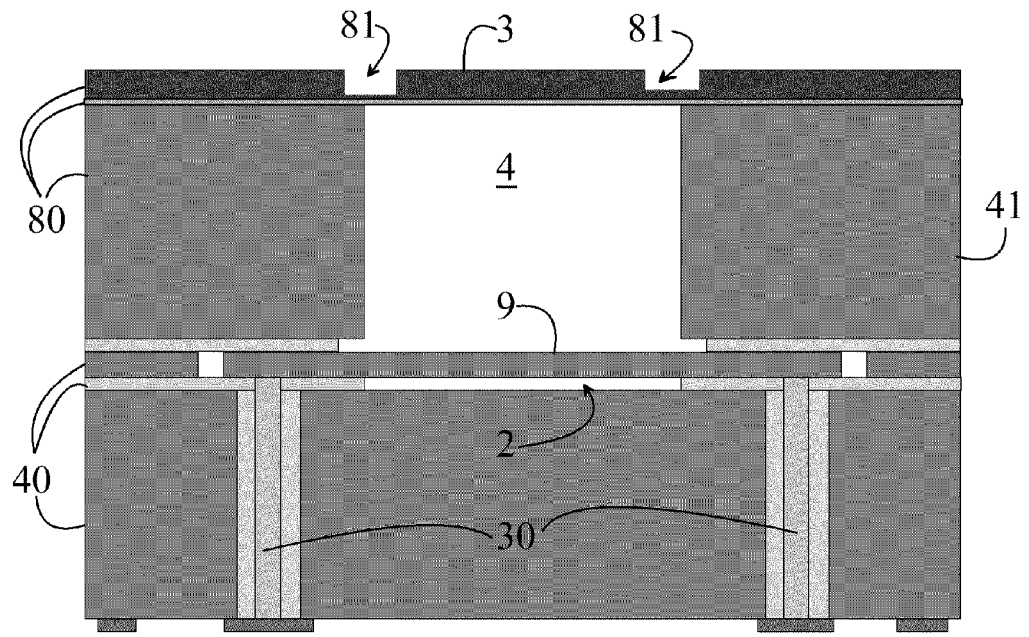
FIG. 5 shows a cross-sectional side view of an alternative construction of the sensor according to the invention.

FIG. 5 shows a sensor, in which the ultrasound cavity 4 is formed by bonding two SOI discs 40 and 80 to each other. A cavity 4 is etched into the upper SOI disc 80. This cover silicon is then polished and thinning grooves 81 are made in it, to permit the diaphragm 3 to make a piston-like movement. Thus, the upper silicon 3 in the upper SOI disc 80 forms a moving measuring diaphragm and the lower 41 a gas cavity 4.

Figure 7:
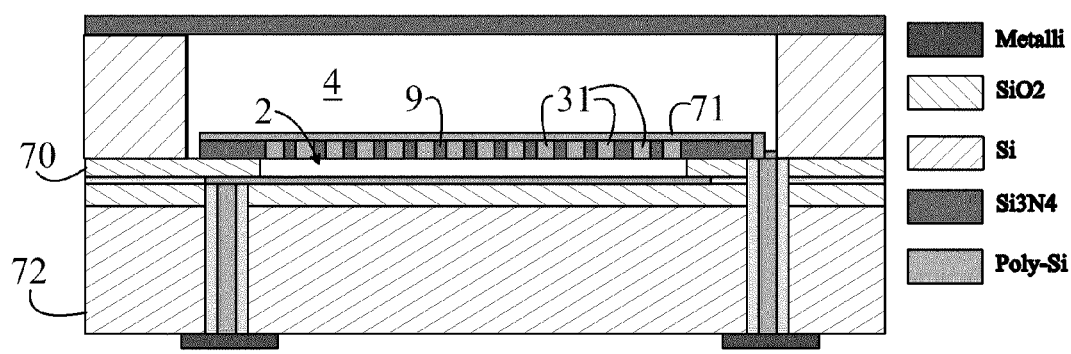
FIG. 7 shows a cross-sectional side view of an alternative construction of the sensor according to the invention.

According to FIG. 7, the sensor according to the invention is based on a surface micromechanical construction, in which the basic structure is a silicon disc 72. In the construction, a silicon-oxide layer 70 is grown on top of the silicon disc and a thin nitride diaphragm 9, in which holes 31 are etched, is grown on top of it. Porous polysilicon 71 is grown on top of the nitride. Silicon oxide 70 is etched through the porous polysilicon 71, which creates a cavity 2. After this, the porous polysilicon 71 is filled by growing additional polysilicon. The pressure of the cavity of the transmitter 2 can be determined at this stage. The spring constant of the diaphragm 9 is determined by the tensile stress of the nitride and can be adjusted by altering the process parameters. An electrical connection is made by etching a hole through the SOI disc 40 and growing an insulating oxide and conductive polysilicon in the hole. The sound cavity 4 is made in the same way as in the SOI disc example of FIG. 3.

The construction can be manufactured in many different ways. For example, the ultrasound transmitter can be made by growing a polysilicon diaphragm on top of silicon and silicon oxide, and then etching away the silicon oxide from a specific area through holes made in the polysilicon. This permits the manufacture of a low-mass ultrasound transmitter, in which case we can more easily make the cavity determine the effective losses of the entire construction. On the other hand, the ultrasound sensor can be formed of several, e.g., hexagonal transmitters, whereby we can adjust a suitable operating frequency by the size of an individual element and determine the surface area of the cavity. This type of construction is advantageous also because it permits a construction, in which the frequency is high and the cavity wide, and thus the upper diaphragm will not so easily radiate the ultrasound away through the diaphragm of the cavity, thus reducing the resolution.

FIG. 3 shows an acceleration sensor, in which the mass is especially thick. In this example, a very high frequency (e.g. 2 Mhz) is used, so that the ultrasound cavity can be very low and an upper cavity is not required. In the sensor in question, it is, of course, sensible to divide the transmitter into several parts (not shown in the figure).

The accompanying description of the invention has presented only some characteristic features of the invention. It is obvious that embodiments of the invention can vary even widely within the scope of the set of claims.

Thus, in the invention the interaction of an ultrasound transmitter and a cavity connected to it is measured. For its part, the cavity is sensitive to the variable being measured, through its passive sensor diaphragm 9, or the properties of the gas contained in the cavity.

According to the invention, the cavity 4 can be part of a device case, for example, in a pressure-sensor application part of the glass of a diver's watch can be the element transmitting the pressure. Correspondingly, in microphone applications the cavity 4 can be part of the shell of a telephone, etc. Such a form of casing can also be possible, in which an ultrasound circuit according to the invention is on a circuit card and the cavity is formed of a case, which is attached to the circuit card.

The invention claimed is:

1. A sensor for measuring pressure, variation in sound pressure, a magnetic field, acceleration, vibration, or the composition of a gas, said sensor comprising:
   an ultrasound transmitter, and
   a cavity arranged in connection with the ultrasound transmitter, which is in resonance mode at the ultrasound frequency used,
   wherein the sensor comprises a flexible diaphragm, the distance of the flexible diaphragm from the ultrasound transmitter being selected in such a way that the resonance condition is met, the flexible diaphragm being located at the opposite end of the cavity with respect to the ultrasound transmitter,
   wherein the ultrasound transmitter comprises a diaphragm oscillator, which is connected to a medium around the sensor,
   wherein the sensor is configured to measure the interaction between the ultrasound transmitter and the cavity, and
   wherein a reflector cavity is arranged on top of the cavity, in order to increase the sensitivity of the sensor.

2. The sensor according to claim 1, wherein the sensor comprises a measuring device for measuring the interaction between the ultrasound transmitter and the cavity, which comprises a power-measurement device.

3. The sensor according to claim 1 or 2, wherein the sensor is formed using MEMS technology, in such a way that there is a pressure inside the ultrasound transmitter.

4. The sensor according to claim 1, wherein the sensor is a surface micromechanical structure formed on an SOI disc.

5. The sensor according to claim 1, wherein, in the non-deformed state, the distance between the ultrasound transmitter and the sensor element is one quarter, one half, or a multiple of these, of the wavelength of the ultrasound frequency used.

6. The sensor according to claim 1, wherein the cavity is connected to the environment by a gas-permeable structure, in order to permit the measurement of gas content.

7. The sensor according to claim 1, wherein an additional mass is located in the cavity, for the measurement of acceleration.

8. The sensor according to claim 1, wherein a current-transporting coil is located in the flexible diaphragm, for the measurement of a magnetic field.

9. The sensor according to claim 1, wherein the sensor element is on the outer surface of a device case.

10. The sensor according to claim 9, wherein the outer surface of the device case of the device, connected to the sensor, forms at least part of the sensor.

11. The sensor according to claim 9, wherein the device case is a device case of a mobile telephone or watch.

12. A method for measuring pressure, variation in sound pressure, a magnetic field, acceleration, vibration, or the composition of a gas, in which method
an ultrasound transmitter is used to create ultrasound in a cavity, which is in resonance mode at the ultrasound frequency used,
and
a flexible diaphragm, the distance of the flexible diaphragm from the ultrasound transmitter is selected in such a way that the resonance condition is met, is located at the opposite end of the cavity to the ultrasound transmitter,
a device, in which there is a diaphragm oscillator, which is connected to a medium around the sensor, is used as the ultrasound transmitter,
the interaction between the ultrasound transmitter and the cavity is used to determine a desired variable, and
wherein a reflector cavity is arranged on top of the cavity, in order to increase the sensitivity of the sensor.

13. The method according to claim 12, wherein the interaction between the ultrasound transmitter and the cavity is implemented by measuring the power drawn by the ultrasound transmitter.

14. The method according to claim 12 or 13, wherein the sensor is formed using MEMS technology, in such a way that there is a pressure inside the ultrasound transmitter.

15. The method according to claim 12, wherein the device is formed on an SOI disc.

16. The method according to claim 12, wherein, in a non-deformed state, one quarter, one half, or a multiple of these of the wavelength of the ultrasound frequency is used as the distance between the ultrasound transmitter and the sensor element.

17. The method according to claim 12, wherein the cavity is connected to the environment by a structure permeable to the gas being measured, in order to permit measurement of the gas content.

18. The method according to claim 12, wherein an additional mass, for measuring acceleration, is located in the cavity.

19. The method according to claim 12, wherein a coil transporting current is located in the flexible diaphragm, in order to measure a magnetic field.

20. The method according to claim 12, wherein the sensor element is located on the outer surface of a device case, so that it can be used as part of the interface.

21. The method according to claim 20, wherein the outer surface of the device case of the device, connected to the sensor, is used as at least part of the sensor.

22. The method according to claim 20, wherein the device case is a case for a mobile telephone.

23. A method of measuring a gas content, comprising using the sensor according to claim 1.

24. A method of measuring a magnetic field, comprising using the sensor according to claim 1.

25. A method of measuring pressure, comprising using the sensor according to claim 1.

26. A method of measuring distance, comprising using the sensor according to claim 1.

27. A method of detecting sound, comprising using the sensor of claim 1 as a microphone.

28. A method of measuring acceleration, comprising using the sensor of claim 1.

* * * * *